(12) United States Patent
Dennis

(10) Patent No.: US 8,926,665 B2
(45) Date of Patent: Jan. 6, 2015

(54) CORTICAL, ANTI-MIGRATION, FACET DOWEL FOR FUSION OF FACET JOINTS IN THE SPINE AND DEVICES FOR SETTING THE SAME IN PLACE

(75) Inventor: M. David Dennis, San Antonio, TX (US)

(73) Assignee: FacSecure, LLC, San Antonio, TX (US)

( * ) Notice: Subject to any disclaimer, the term of this patent is extended or adjusted under 35 U.S.C. 154(b) by 272 days.

(21) Appl. No.: 13/051,488

(22) Filed: Mar. 18, 2011

(65) Prior Publication Data
US 2011/0230912 A1 Sep. 22, 2011

Related U.S. Application Data

(60) Provisional application No. 61/315,071, filed on Mar. 18, 2010.

(51) Int. Cl.
  A61B 17/70 (2006.01)
  A61B 17/16 (2006.01)
  A61B 17/88 (2006.01)

(52) U.S. Cl.
  CPC ......... *A61B 17/7064* (2013.01); *A61B 17/1671* (2013.01); *A61B 17/8897* (2013.01)
  USPC ....................................................... 606/247

(58) Field of Classification Search
  USPC ...................... 606/246–249; 623/17.11–17.16
  See application file for complete search history.

(56) References Cited

U.S. PATENT DOCUMENTS

| | | | |
|---|---|---|---|
| 5,306,307 A * | 4/1994 | Senter et al. | 623/17.16 |
| 6,080,155 A | 6/2000 | Michelson | |
| 6,436,098 B1 | 8/2002 | Michelson | |
| 6,966,930 B2 * | 11/2005 | Arnin et al. | 623/17.11 |
| 7,001,433 B2 * | 2/2006 | Songer et al. | 623/17.16 |
| 7,300,465 B2 | 11/2007 | Paul et al. | |
| 7,708,761 B2 | 5/2010 | Peterso | |
| D629,904 S | 12/2010 | Horton | |
| 7,854,767 B2 | 12/2010 | May et al. | |
| 7,867,277 B1 | 1/2011 | Tohmeh | |
| 7,887,596 B2 | 2/2011 | Douget et al. | |
| 7,892,286 B2 | 2/2011 | Michelson | |
| 7,901,439 B2 | 3/2011 | Horton | |
| 7,963,991 B2 * | 6/2011 | Conner et al. | 623/17.11 |
| 8,083,798 B2 * | 12/2011 | Allard et al. | 623/17.16 |
| 8,425,558 B2 * | 4/2013 | McCormack et al. | 606/247 |
| 2006/0036323 A1 * | 2/2006 | Carl et al. | 623/17.11 |
| 2006/0276790 A1 * | 12/2006 | Dawson et al. | 606/61 |
| 2008/0234758 A1 * | 9/2008 | Fisher et al. | 606/309 |
| 2009/0270989 A1 * | 10/2009 | Conner et al. | 623/17.16 |
| 2010/0185287 A1 * | 7/2010 | Allard et al. | 623/17.11 |
| 2011/0313465 A1 * | 12/2011 | Warren et al. | 606/279 |
| 2012/0109197 A1 * | 5/2012 | Carl et al. | 606/247 |

\* cited by examiner

*Primary Examiner* — Jan Christopher Merene
*Assistant Examiner* — Steven Cotroneo
(74) *Attorney, Agent, or Firm* — Jackson Walker, LLP

(57) ABSTRACT

A novel allograft is provided for insertion into a prepared site between adjacent spinal facets. The allograft or facet dowel is typically comprised of three portions, a partially spherical body defining a spherical segment, a nose portion, and a tail portion, all aligned along a longitudinal axis. In addition, a set of instruments is provided for the excavation of an allograft placement site between the two facets. The set of instruments includes a T-spade drill which will, in conjunction with a normal drill, excavate a site for the emplacement of the allograft. A novel method of using the instruments and the allograft is also provided.

26 Claims, 20 Drawing Sheets

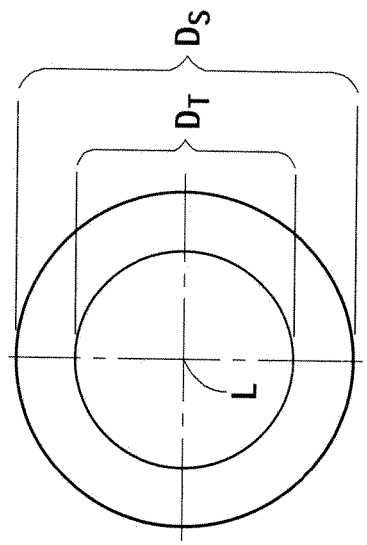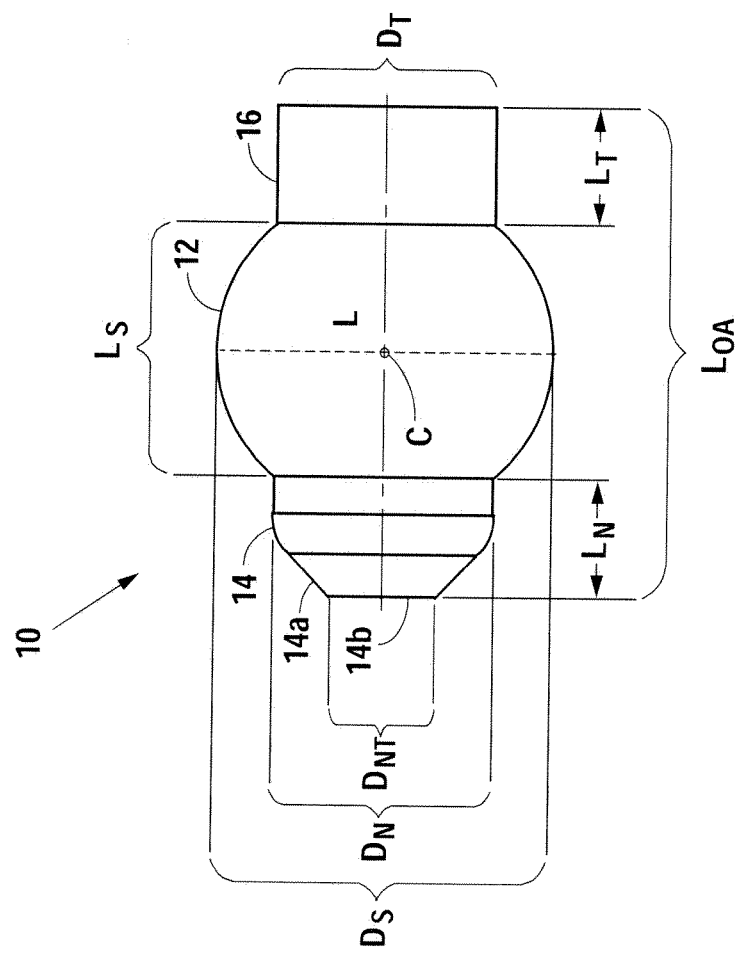

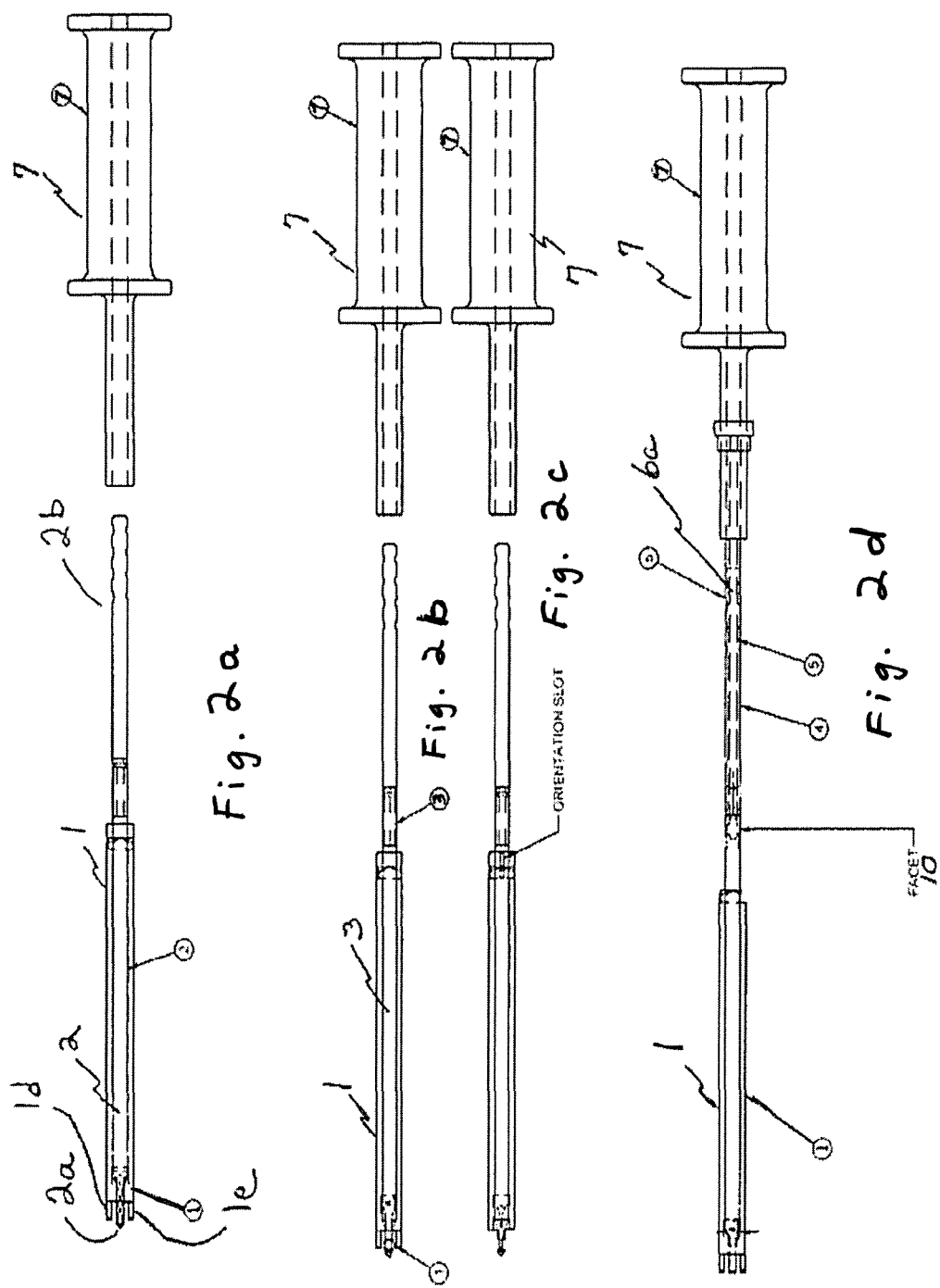

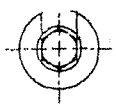
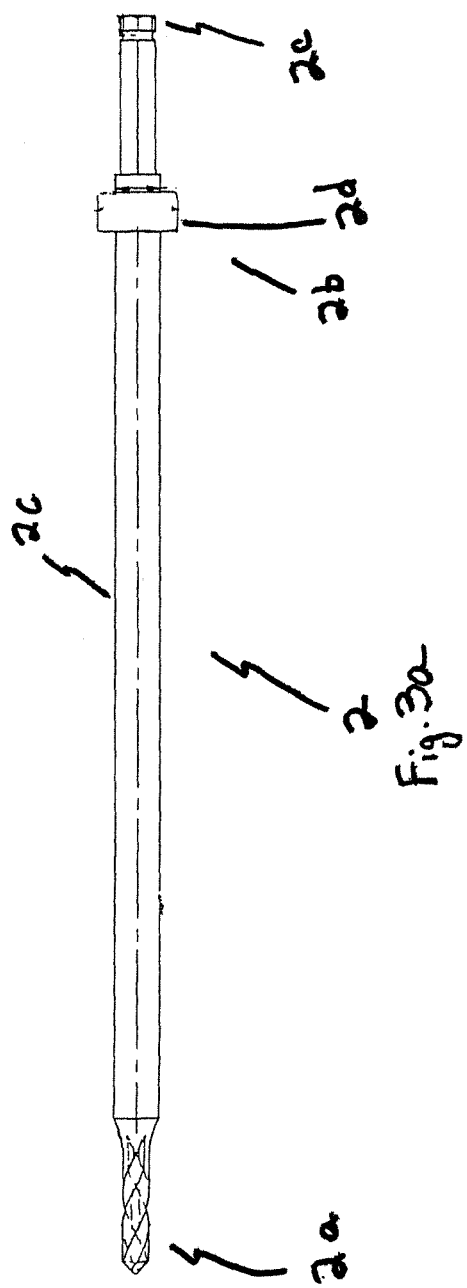
Fig. 3b
Fig. 3a

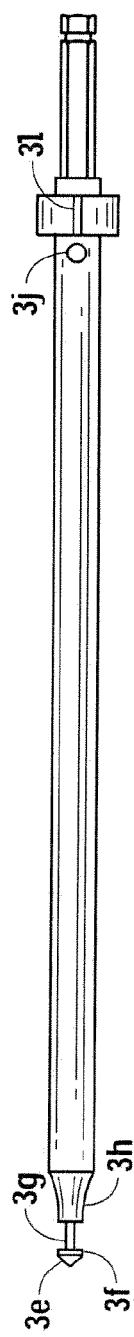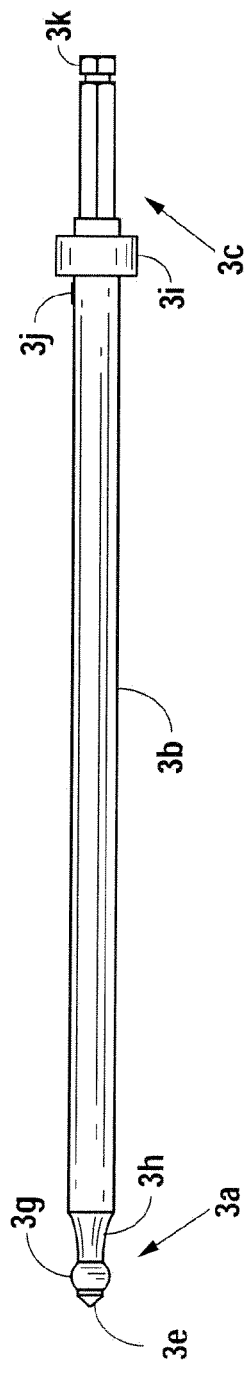

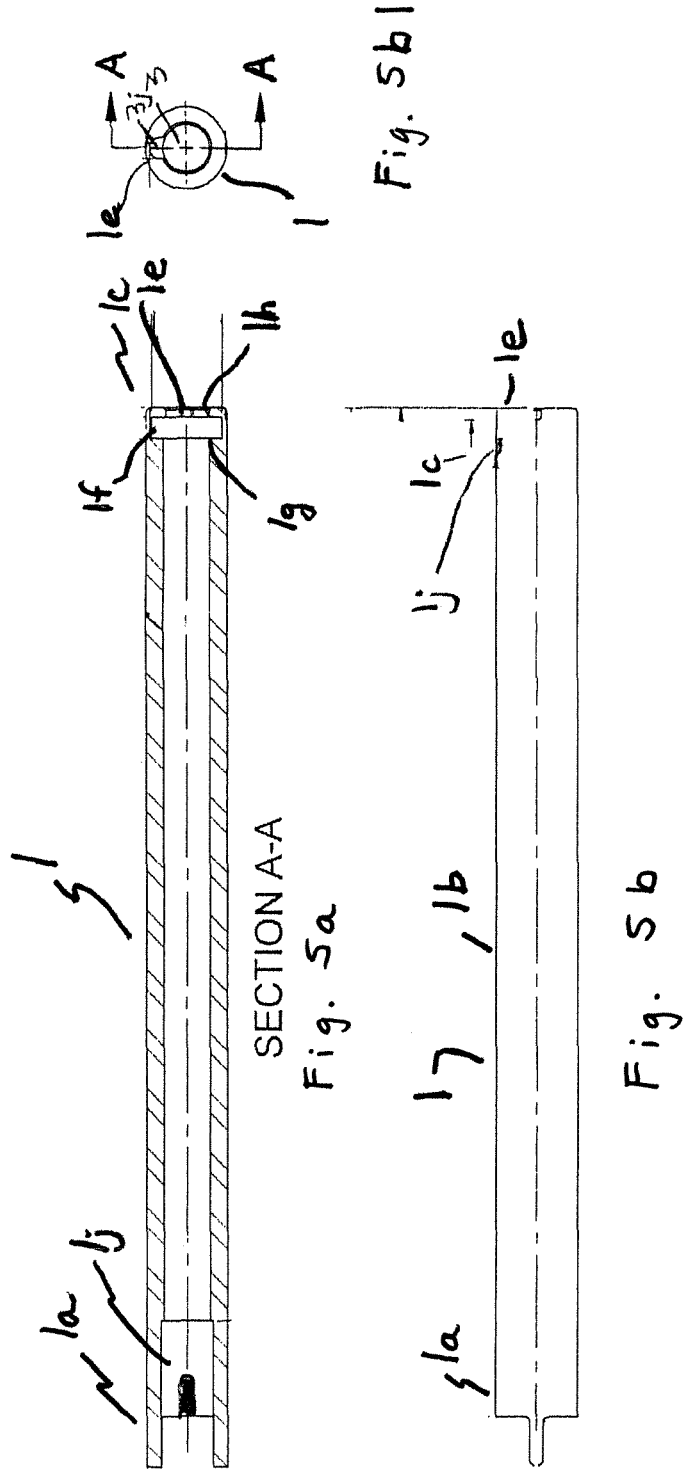

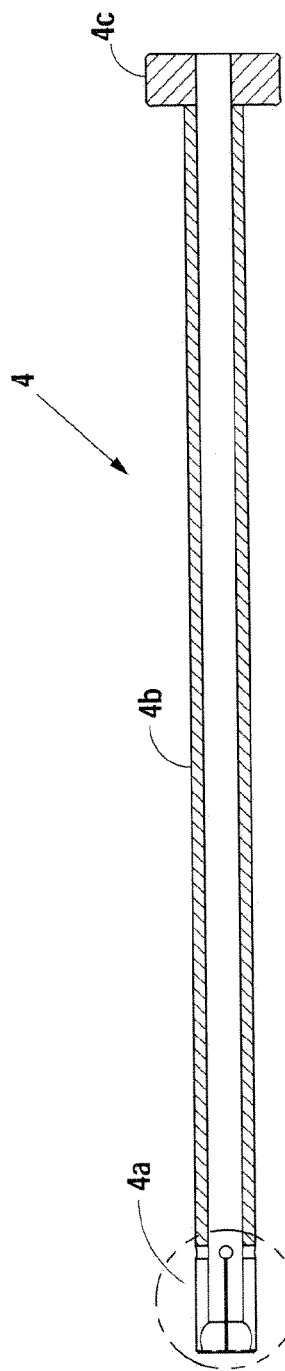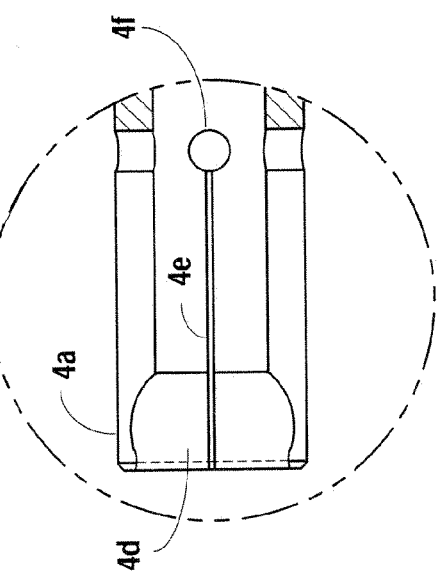
Fig. 6a
Fig. 6b

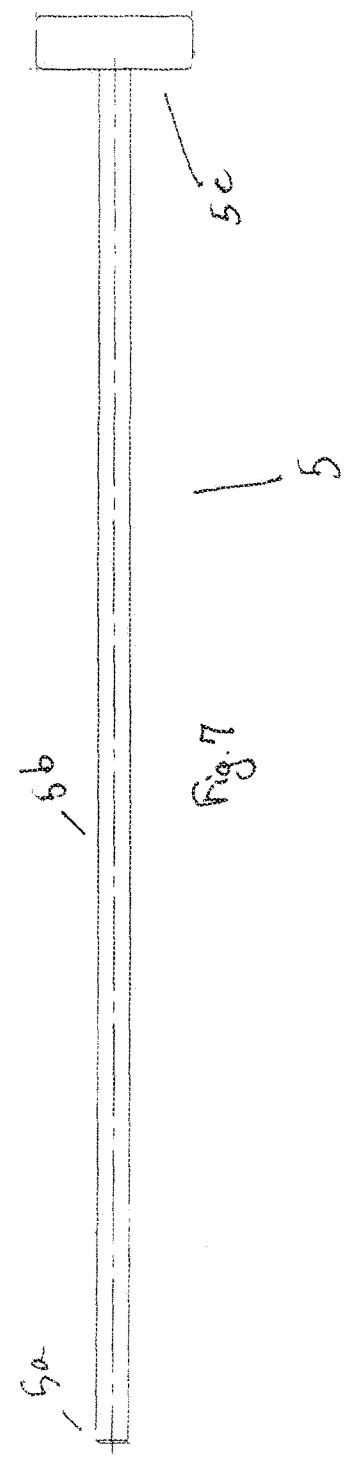

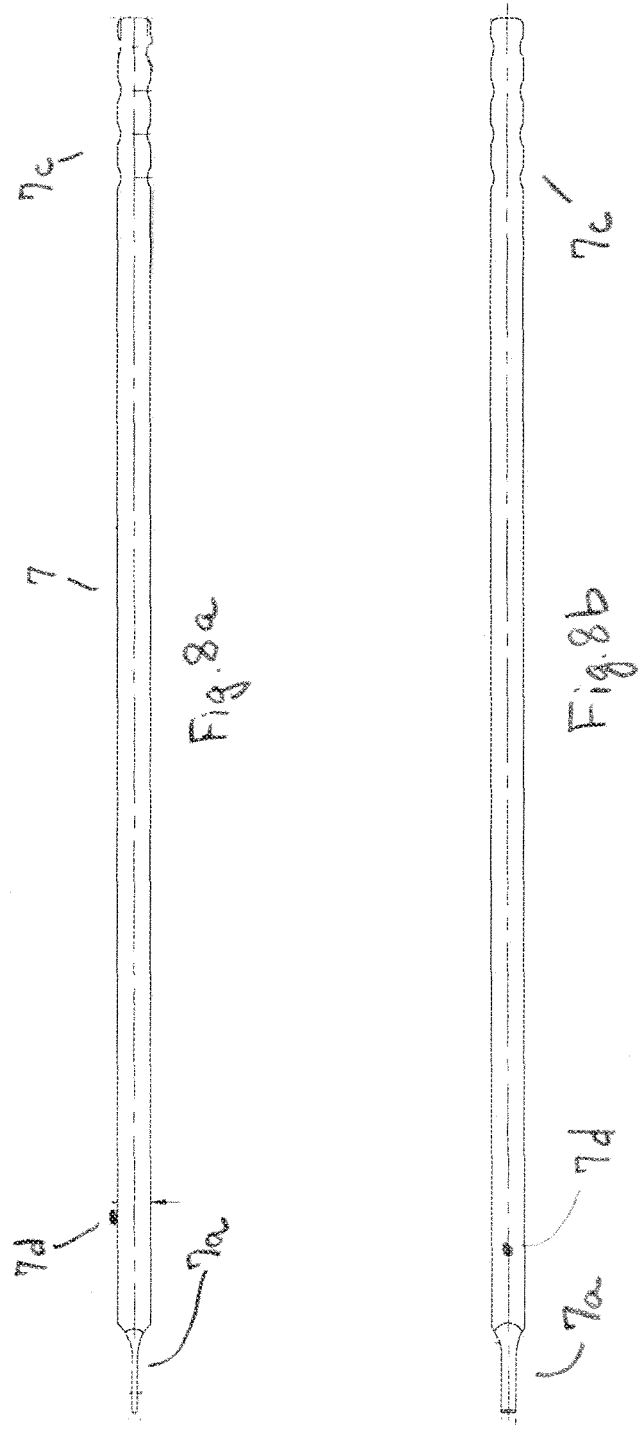

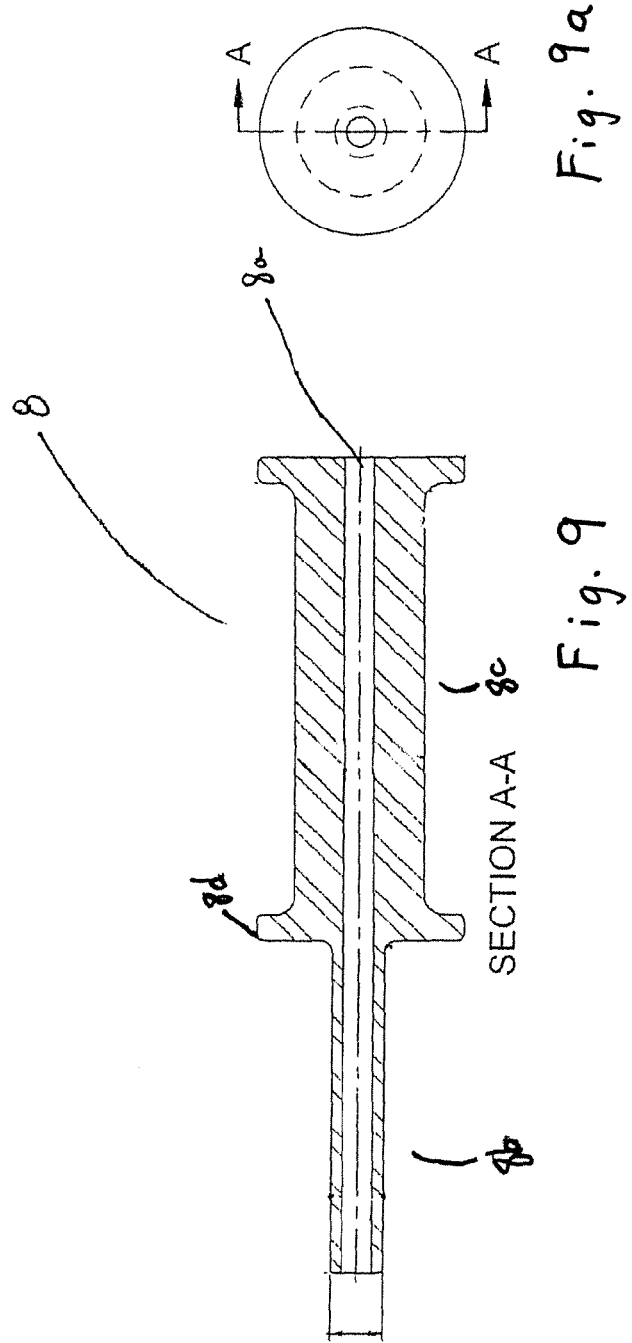

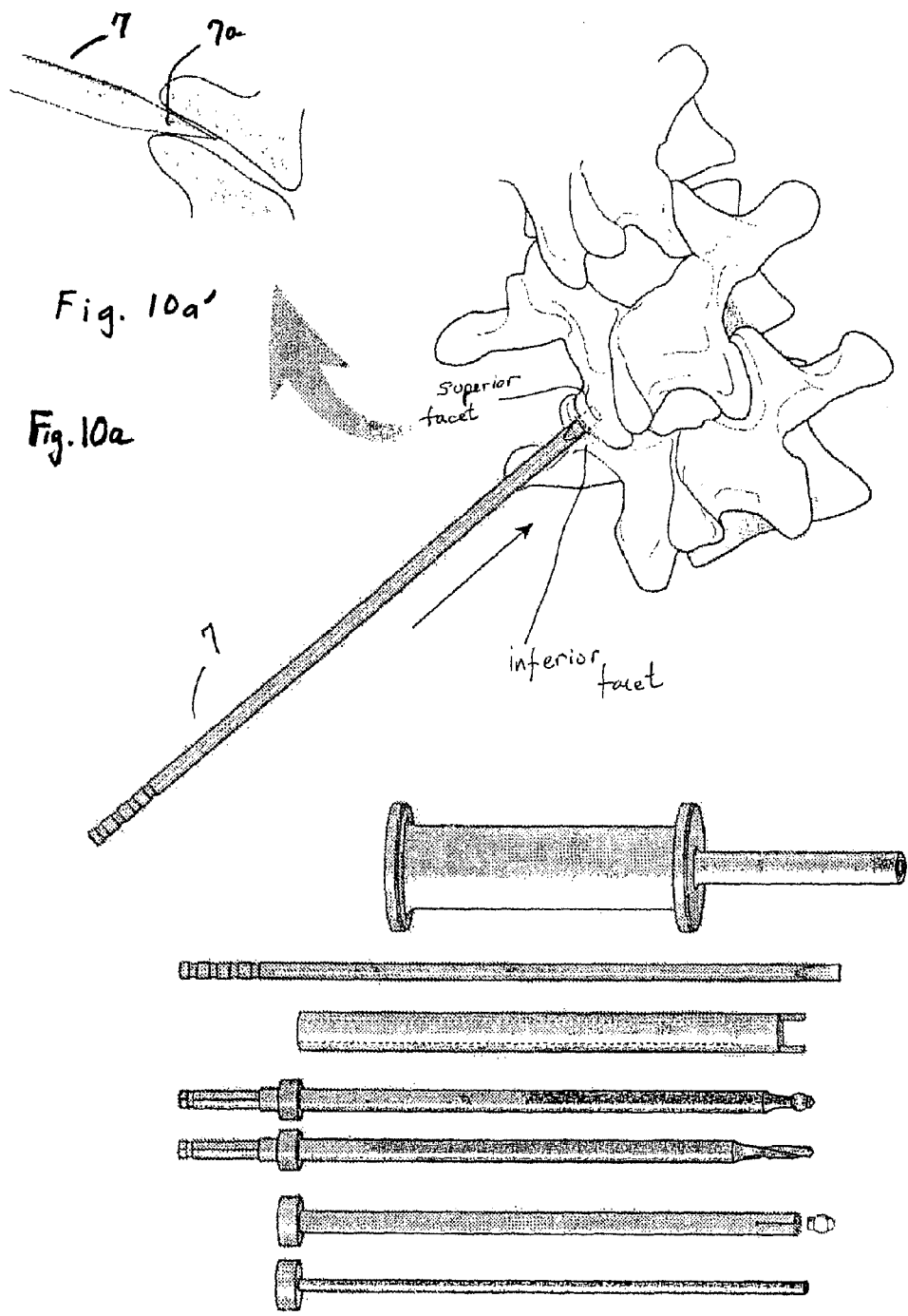

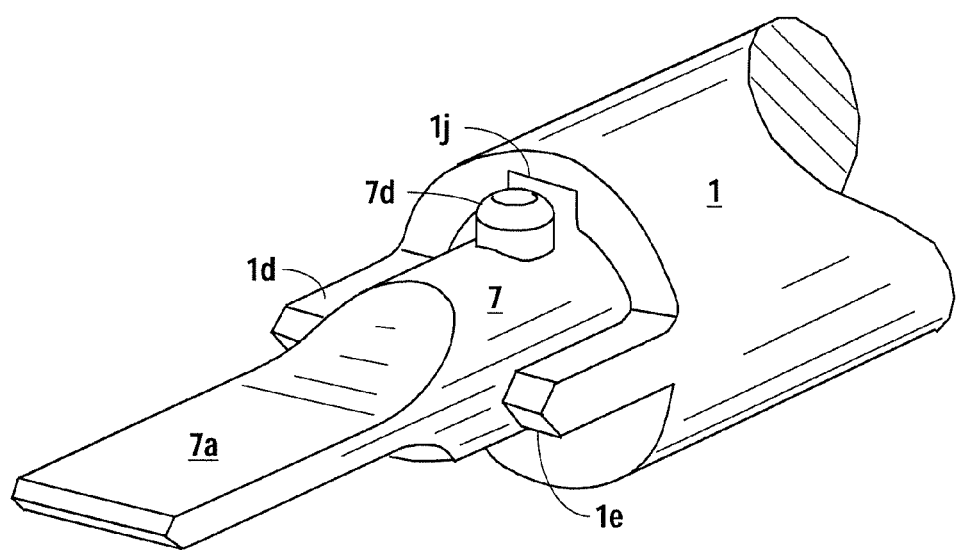
Fig. 10b1

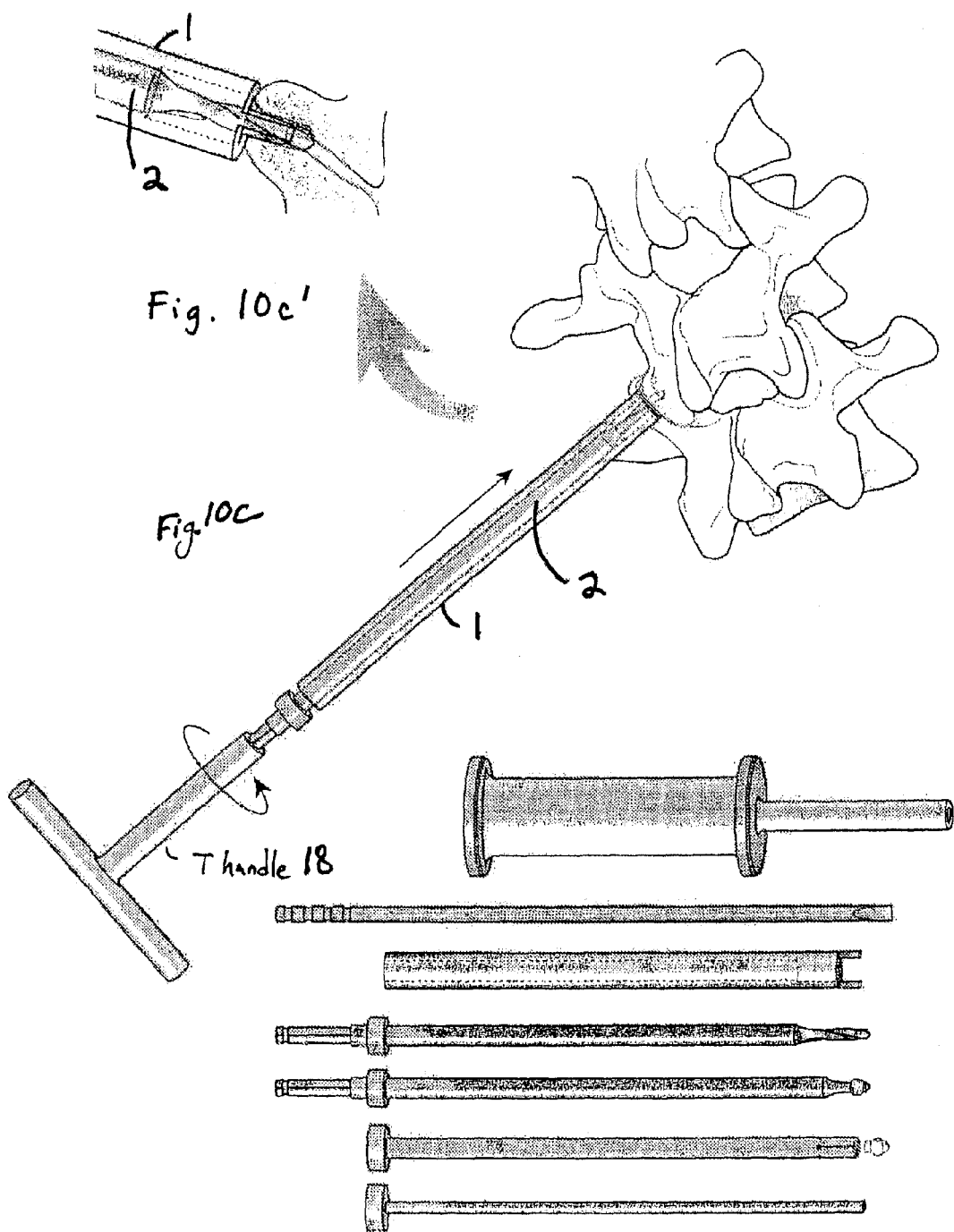

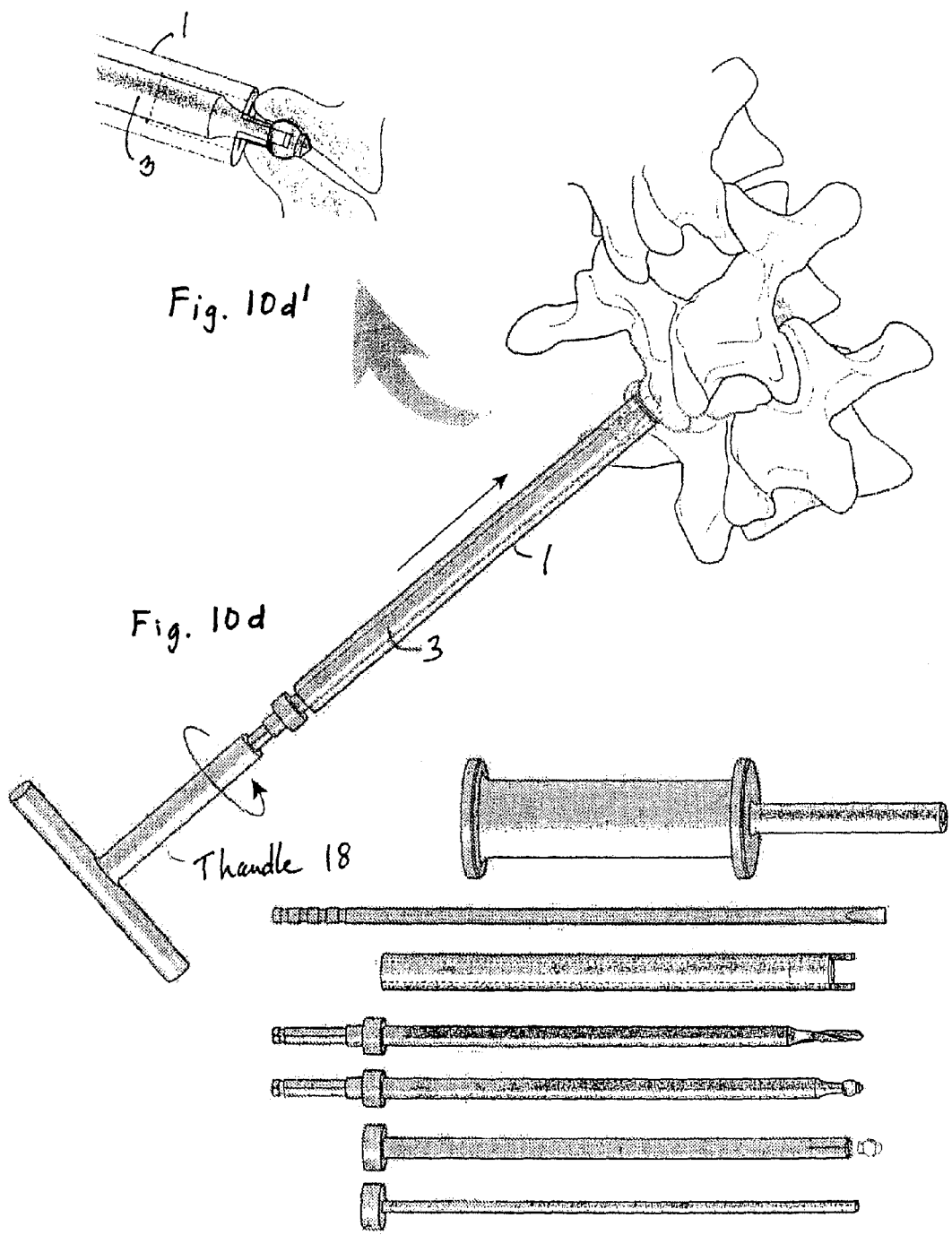

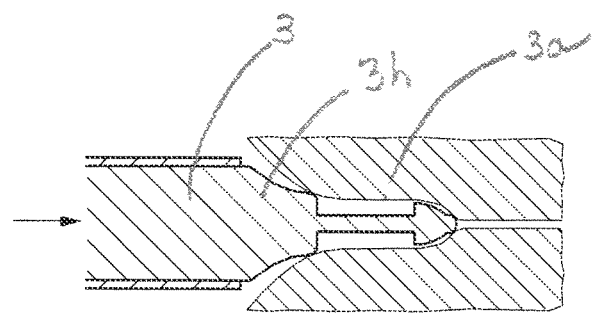
Fig.10d1
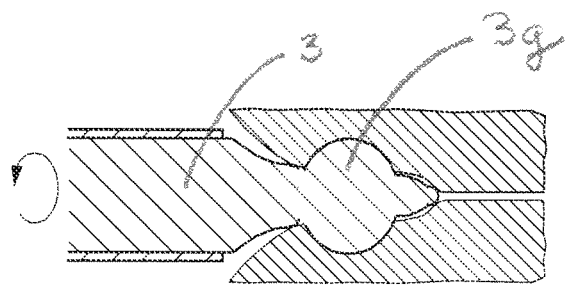
Fig.10d2
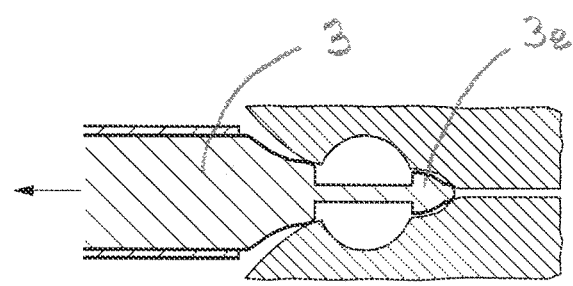
Fig.10d3

CORTICAL, ANTI-MIGRATION, FACET DOWEL FOR FUSION OF FACET JOINTS IN THE SPINE AND DEVICES FOR SETTING THE SAME IN PLACE

This application claims the benefit of Provisional Patent Application Ser. No. 61/315,071, filed Mar. 18, 2010.

FIELD OF THE INVENTION

Facet dowel allografts and devices for emplacement of the same, more specifically, for emplacement of a facet dowel allograft for fusion of facet joints in the open surgery of the spine.

BACKGROUND OF THE INVENTION

Millions of Americans suffer from lower back pain. For facet joint disorders, often the source of lower back pain, the most commonly used procedure for alleviating the pain is facet fusion.

It is one objective in a facet spinal fusion procedure to reduce a patient's post-operative pain, blood loss, and rehab time. An important consideration in achieving these foregoing objectives is an allograft that ensures vertebrae stability and is resistant to graft migration.

OBJECTS OF THE INVENTION

It is an one of the objects of this invention to provide for a facet dowel allograft that is stable and helps prevent allograft migration after implanting.

It is another object of the present invention to provide for a set of instruments that will help prepare the adjacent facets for receipt of the novel dowel and to emplace the novel dowel in an open surgical operation between the adjacent facets.

SUMMARY OF THE INVENTION

A novel allograft is provided for insertion into a prepared site between adjacent facets, the allograft or facet dowel typically comprised of three portions, a partially spherical body defining a spherical segment, a nose portion, and a tail portion, all aligned along a longitudinal axis. In addition, a set of instruments is provided for the excavation of an allograft and placement site between the two facets. The set of instruments includes a T-spade drill which will, in conjunction with a normal drill, excavate a site for the emplacement of the allograft. A novel method of using the instruments and the allograft is also provided.

The novel facet dowel is typically comprised of 100% cortical bone, but may, in an alternate embodiment, be comprised of cancellus bone. The facet dowel typically is comprised of three portions in an integrated body having a long axis; a partially spherical body defining a spherical segment, a nose portion along the long axis thereof and a tail portion extending along the long axis thereof.

BRIEF DESCRIPTION OF THE DRAWINGS

FIGS. 1A and 1B illustrate a facet dowel allograft.
FIGS. 1C and 10 illustrate alternate embodiments of the implant.
FIGS. 2A, 2B, 2C, and 2D are views of various instruments used in the placement of the novel dowel illustrated in FIGS. 1A-10D in a facet fusion procedure.

FIGS. 3A and 3B illustrate side and end views of the prep-drill for use in the facet fusion procedure.

FIGS. 4A, 48, and 4C illustrate side, top, and end views of the T-spade drill of Applicants' present device.

FIGS. 5A, 5B, and 5B1 illustrate top (cutaway), side, and removed end views of the working channel of Applicants' present device.

FIGS. 6A and 6B illustrate cross-sectional side and detailed end views of the inserter of Applicants' present device.

FIG. 7 illustrates a side elevational view of a tamp driver for use with Applicant's present invention.

FIGS. 8 and 8B illustrate side and top views of a joint finder for use with Applicant's devices.

FIGS. 9 and 9a illustrate a channel set for use with Applicant's present device.

FIGS. 10A, 1B, 10B1, 10C, 10D, 10D1, 10D2, 10D3, 10E, and 10F illustrate perspective views of the novel instruments in use, in "step by step" fashion.

FIGS. 10a', 10b', 10c', 10d', 10e', and 10f' illustrate respective exploded views of FIGS.

10a, 10b, 10c, 10d, 10e, and 10f, showing the interaction of the instruments with the facet joint.

Figure 11:
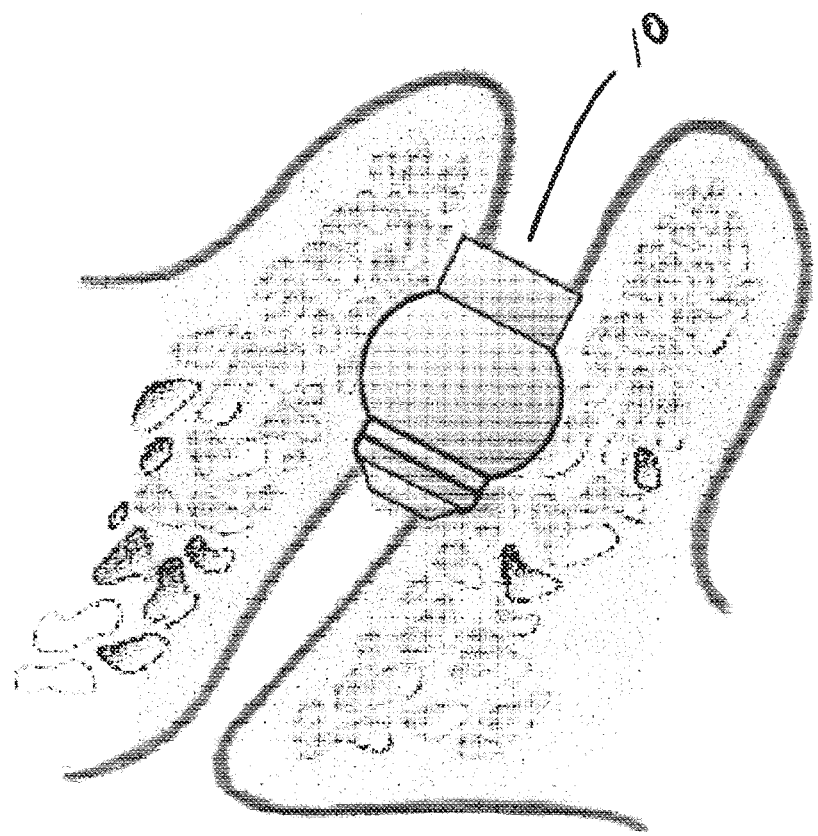

FIG. 11 illustrates an allograft implanted in a facet joint.

DETAILED DESCRIPTION OF THE PREFERRED EMBODIMENT

FIGS. 1A and 1B illustrate a facet dowel allograft 10 in side view and rear view. Facet dowel allograft 10 is seen to comprise, typically, three portions. A body portion 12 is partially spherical or a spherical segment. A nose portion 14 and a tail portion 16 extend along a longitudinal axis L, which longitudinal axis L extends through a spherical center point C of the body portion. Body portion 12 is partially spherical and the sphere is truncated by parallel planes with a nose portion 14 extending in a first direction along a longitudinal axis L and a tail portion 16 extending opposite in a second direction along the same longitudinal axis L.

Nose portion 14 is seen to include a least some tapered walls 14a, which define a rounded, cap-like or core-like structure, which may have a tip portion 14b. Nose portion is typically partly cylindrical with a larger diameter $D_N$ where it joins body portion 12 and a smaller diameter $D_{NT}$ at a tip portion 14b thereof.

Tail portion 16 may be at least partly cylindrical and may have a diameter of $D_T$. $D_T$ is usually equal to or approximately equal to $D_N$. $D_N$ and $D_T$ are typically smaller than diameter $D_S$, which is the diameter of the body portion or spherical segment 12 of the implant or allograft 10.

Figure 1C:
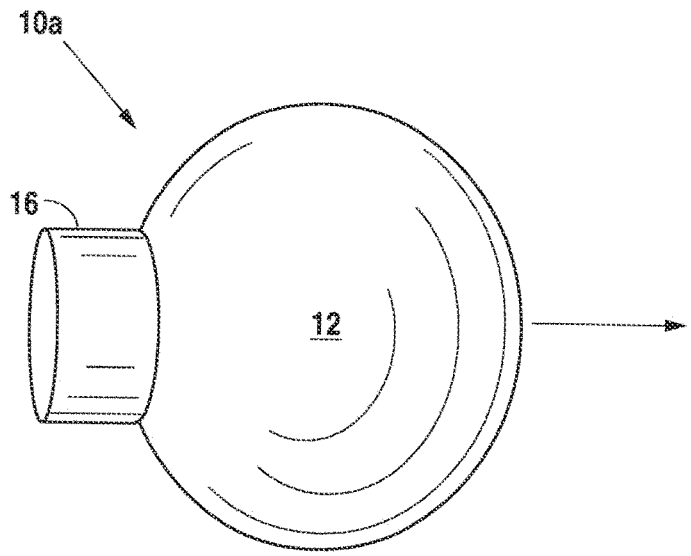

FIG. 1C illustrates an alternate embodiment of Applicants' allograft or implant 10a that omits the nose portion. In other words, spherical body 12a continues in its spherical shape where, in the prior embodiments, there was a nose portion.

Figure 1D:
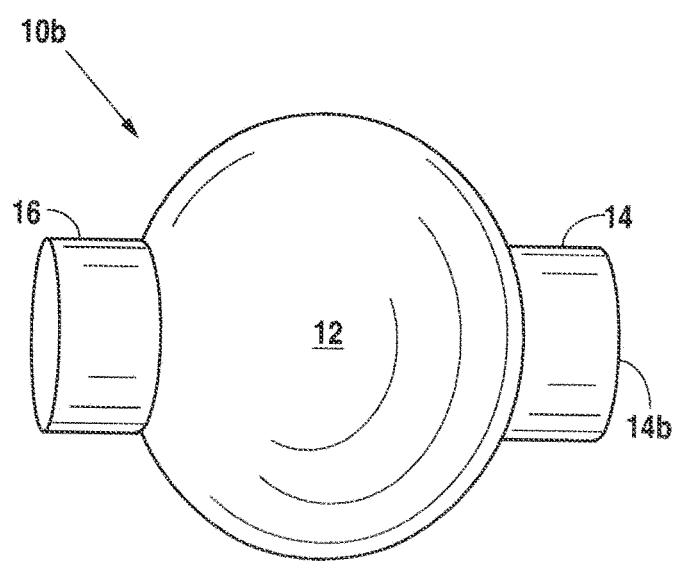

FIG. 1D illustrates an alternate preferred embodiment of Applicants' allograft or implant 10b, wherein the nose portion 14 does not have a cap shape to it, instead is truncated with a flat nose tip 14b.

| RANGE/PREFERRED ALLOGRAFT DIMENSIONS | | |
|---|---|---|
| | RANGE | PREFERRED |
| $L_{OA}$ | 6.5 mm-10.5 mm | 8.5 mm |
| $L_N$ | 1-3 mm | 2 mm |
| $L_S$ | 2.5-6.5 mm | 4.5 mm |
| $L_T$ | 1-3 mm | 2 mm |
| $D_N$ | 1.8-5.8 mm | 3.8 mm |
| $D_S$ | 3.8-7.8 mm | 5.8 mm |
| $D_T$ | 1.8-5.8 mm | 3.8 mm |
| $D_{NT}$ | .8-3.8 mm | 1.8 mm |

FIGS. 2A, 2B, 2C, and 2D will be referred to next. These figures help illustrate the structure, function, and use of the instruments for and placement of, the novel dowels illustrated in FIGS. 1A-1D in a facet fusion procedure.

FIGS. 2A-2D show a cylindrical hollow working channel 1 having two spaced apart legs 1d/1e. In FIG. 2A, working channel receives a prep-drill 2, which prep-drill will drill out an inter-facet site for the allograft emplacement. Prep-drill 2 has a working shaft tip 2a of a diameter equal to about $D_N$ (may be slightly smaller or slightly larger) and tapered to a point. The tapered end of drill may taper at about the same angle of the end walls of the cap of the nose of allograft 10. It engages a T-handle 18 (see FIG. 10C) at the removed end thereof and is rotated. Tip or working portion is designated 2a and removed end 2b.

After the allograft site is selected and drilled out in ways known in the art, the prep-drill is removed from the working channel 1 and a T-spade drill 3 is inserted. It is a function of T spade drill 3 to remove bone adjacent the inter-facet gap for receipt of allograft 10 therein.

FIG. 2B illustrates the T spade drill 3 in working channel 1 in a first position, which may be referred to as the retracted and aligned position, and FIG. 2C illustrates the T spade drill in the same position, but the view being a side view.

When the T spade drill is moved to an extended position from at shown in FIGS. 10D1-10D3, it may be rotated typically 180-360° in the inter-facet location that was previously drilled with the prep-drill to excavate space for the spherical segment of allograft 10. By such rotation, bone is removed from the vertebrae located above and below to define a volume that is spherical with a shape substantially identical to body 12, the volume with a diameter about equal to Ds (see FIG. 1A).

FIG. 2D illustrates the facet or allograft 10, mounted to the tip of inserter 5, which inserter is then slipped into the working channel 1. Then driver tamp shaft 6a is inserted into the hollow channel of inserter 5 as set forth below, to force the allograft 10 into the shaped (drilled and excavated) site.

FIG. 3 illustrates the details of Applicants' prep-drill 2. Prep-drill 2 is seen to have a tip portion 2a, a removed end 2b, and a body 2c. Tip 2a is a working portion of the drill and may have a diameter of about $D_N/D_T$. This diameter is seen to be slightly greater than $D_N$ and $D_T$, which may be about 3.8 mm, but slightly less than diameter $D_S$, which is approximately 5.88 mm.

FIG. 3 also illustrates that removed end 2b may include a stop portion 2d, which will limit the extension of body 2c and tip 2a from the end of working channel as stop portion 2d has a diameter greater than the interior diameter of the working channel. Prep-drill 2 may also have a hex portion 2e at a removed end thereof for engagement with a hex driver which will rotate the prep-drill in a manner known in the art. The length of the working channel and tip to stop portion of prep-drill 2 will be sufficient for the tip 2a of the drill to clear a channel at least the length of the allograft 10.

FIGS. 4A-4C illustrate views of the T spade drill 3; a first view in FIG. 4A and a second view in FIG. 4B, which second view represents a rotation of 90° from the first view of the elongated instrument. Reference to FIGS. 10D1-10D3 is also helpful.

FIGS. 4A and 4B are views of T-spade drill 3. T-spade drill 3 is seen to have a tip portion 3a, a body 3b and a removed end 3c thereof. Body 3b and tip portion 3a are dimensioned to slide within the inner channel of working channel 1 as set forth in FIGS. 2B and 2C.

Turning now to the details of tip portion 3a, tip portion 3a is seen to have a nose portion 3e, which nose portion may have a perimeter 3f and which nose portion joins a body or flat portion 3g. The body or flat portion 3g joins the near end of body 3b, which body may include a tapered portion 3h. The diameter of the nose portion 3e, which is typically tapered, is about equal to the diameter of the working portion 3a of the drill, here about 4.09 mm (may be slightly more or slightly less). The diameter of the flat portion 3g is approximately equal to or slightly greater or slightly less than the diameter of the spherical or segmented portion 12 ($D_N$). This thickness of the flat portion is typically about 1.52 mm or about equal to or slightly more or less than an inter-facet gap at the drill site. The thickness can be seen in FIG. 4A to be less than the diameter of nose $D_N$. Tapered portion 3h usually has a diameter where it meets the flat portion of about $D_N$ (as seen in FIG. 4B). It is seen that, with respect to FIGS. 10D-10D3, the T-spade drill may be inserted in the channel created by the prep-drill with the flat section aligned with the inter-facet gap (and aligned with legs 1d/1e) and, when rotated at least 180-360°, will scoop out a portion of first and second facets to define the inter-facet volume (see FIG. 10D3). This inter-facet volume is partially spherical, substantially similar to the shape of body 12 and having dimensions for the snug receipt of body portion 12 of allograft 10.

Figure 5C:
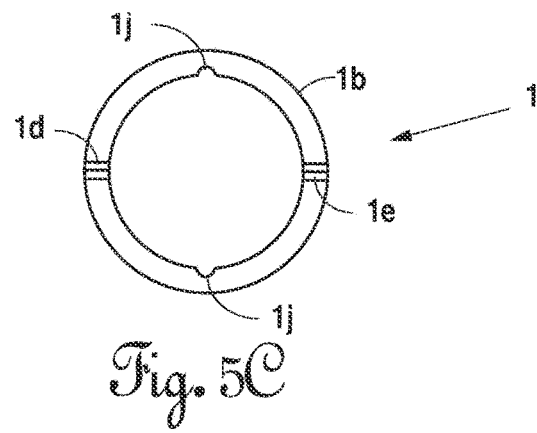
FIG. 5C is an elevational view of the tip portion of the working channel.
Figure 5D:
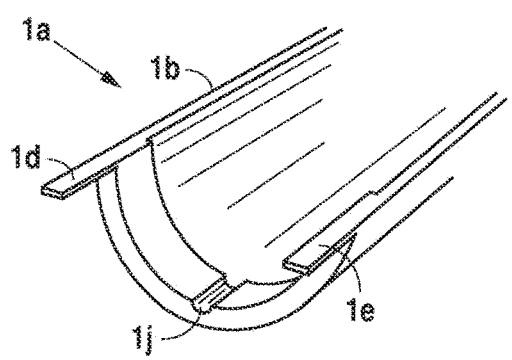
FIGS. 5D and 5E are cutaway cross-sectional longitudinal views of the tip and removed end of the working channel.
Figure 5E:
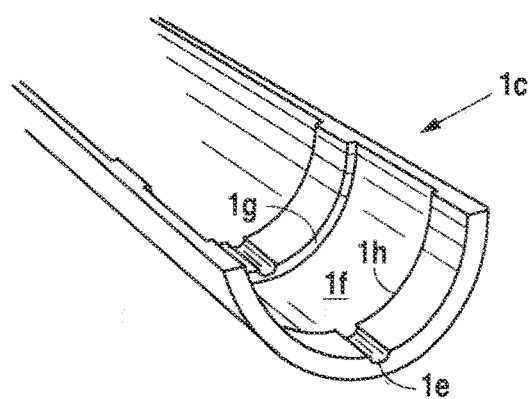

Turning now to removed end 3c, it is seen to include a stop portion 3i which will limit the limit the longitudinal extension of the T-spade drill through the working channel as seen in FIGS. 2B and 2C, as well as a orientation boss 3j. Orientation boss 3j will align with a longitudinal slot 1e in the removed end 1c of working channel 1 as seen in FIGS. 5B and 5E, so that tip portion 3a may move from the position as seen in FIG. 2B (retracted) to the position as seen in FIGS. 10D1 and 10D3, the extended and aligned position. The T-spade drill will not reach the extended position (FIG. 10D) or leave the extended position (i.e., retract) unless the boss 3j is aligned with slot 1e. This ensures that the flat portion 3g is aligned with the channel legs 1d/1e and therefore the gap, as well as aligned with the hole drilled out prior to insertion of the T-spade. A lasered mark 3l on the stop may be aligned with lasered mark 1j on working channel to demonstrate alignment of box 3j and slot 1e. Hex portion 3k will allow the engagement of the T-spade drill 3 with a hex drive tool in ways known in the art. In an alternate preferred embodiment of the T-spade drill 3, a T-shaped handle is integral with the removed end and no hex portion 3k is used. Note that the legs 1d/1e of the working channel and position of longitudinal slot 1e will help place tip 3a aligned in the inter facet gap.

FIGS. 5A-5E illustrate details of working channel 1. Working channel 1 is seen to include a tip portion 1a, a body portion 1b, and a removed end 1c. Working channel 1 will allow the receipt of the prep-drill, T-spade, inserter, and joint finder in ways described herein.

Tip 1a is seen to comprise the pair of legs 1d and 1e, which are spaced apart, as best seen in FIG. 5E. Removed end 1c is seen to include the longitudinal slot 1e to run through inner walls of working channel walls to annular channel 1f, which is defined by shoulders 1g and 1h. Shoulders 1g and 1h will enclose boss 3j as the T-spade drill is rotated from the extended, aligned position as seen in FIGS. 2B and 2C to excavate the two facet joints for the receipt of spherical portion 12 of dowel 10. Moreover, annular channel 1f will be spaced into working channel 1 such that tip 3a of the T-spade drill extends beyond end walls 1i and nose 3e typically beyond the ends of legs 1d/1e of working channel 1.

Figure 10B:
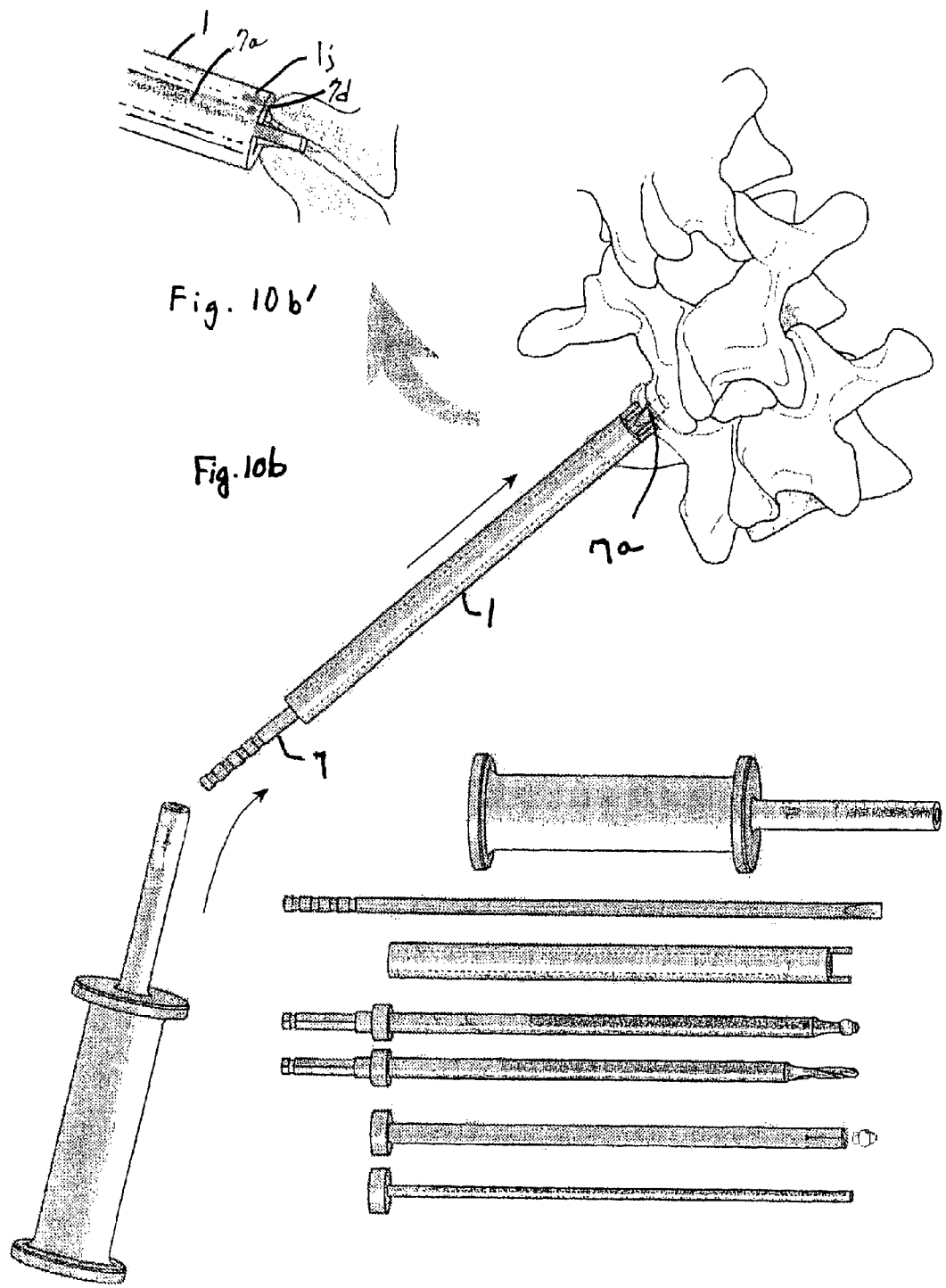

FIG. 5A illustrates a joint finder alignment slot 1j on the inner walls of tip 1a of the working channel 1. It may be seen in FIGS. 8A and 10B1 that there is a boss 7d on the outer surface of the joint finder near tip 1a. When the joint finder locates the joint, the wedge-shaped tip will be properly situated in the joint. The working channel 1 is slid over the joint finder and down the joint finder so legs 1d/1e are next to the joint (the space between the upper and lower facets) until joint finder alignment slot 1j is aligned with boss 7d. When boss 7d and slot 1j are in alignment, then the flat of the tip 7a will be aligned with the two legs of the working channel and the working channel will be properly situated, rotationally-wise in the joint. FIG. 10B1 shows working channel 1 in proper alignment with the seated joint finder (bones have been omitted for clarity), with the working channel 1 in position to drive legs 1d/1e up to a final position that typically puts the legs adjacent the edges of tip 7a and in the joint between the facets.

Legs 1d/1e of the working channel extend about 8 mm beyond the end walls 1i of the working channel 1 and the drill stop 2d puts the tip 2a of the drill 2 about 3 mm beyond the ends of the legs, about the same distance for the T-spade 3. That is to say, the nose of the drill 2 and the nose of the T-spade extend about 3 mm beyond the ends of the legs of the working channel when the either the drill or T-spade stop hits the end walls of the working channel. It may be seen with respect to FIG. 10F that the driver tamp 5, when fully seated in inserter 4 and channel 1, is about 3-4 mm past the ends of the channel set 1.

Figure 10E:
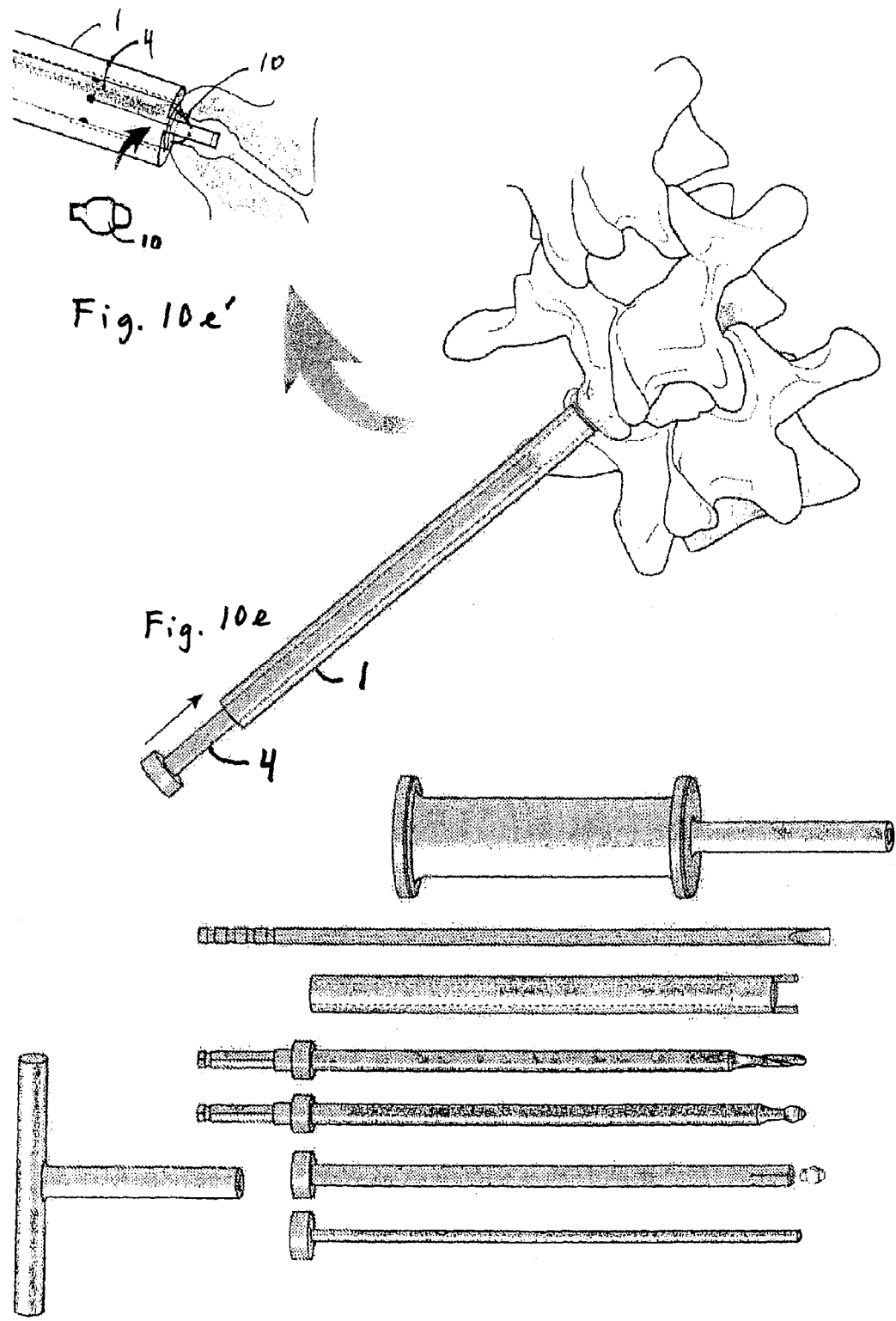
Figure 10F:
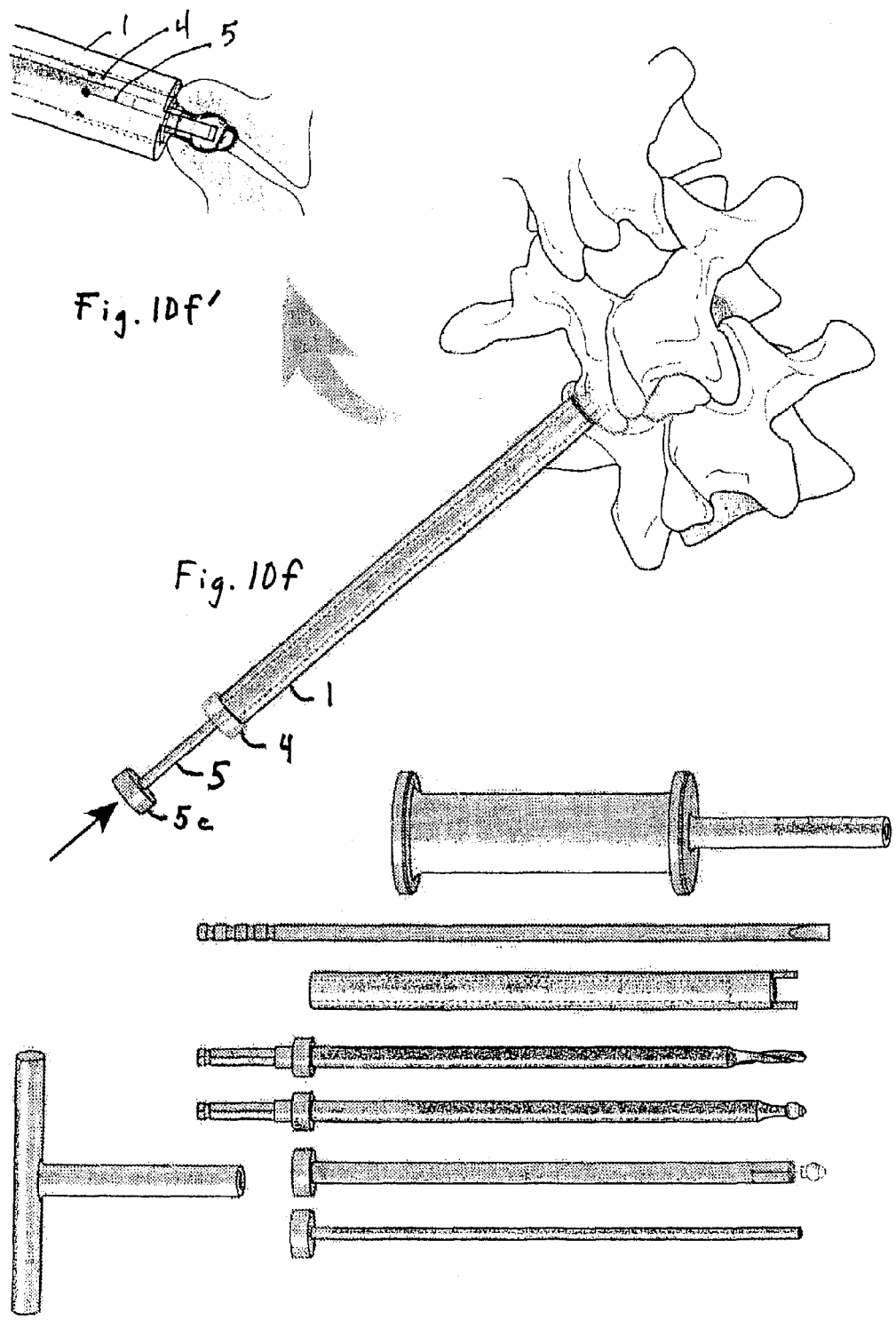

FIGS. 6A and 6B illustrate inserter 4, which functions to firmly engage facet dowel 10 at one end thereof and move, with the facet dowel thereon through the working channel, to the allograft site that has been drilled and shaped (with T-spade 3) as set forth herein. FIGS. 6A and 6B illustrate that inserter 4 includes a tip portion 4a, body portion 4b, and a removed end 4c. Details of tip portion 4a are seen in FIG. 6B. Tip portion 4a includes a partially spherical volume 4d that is dimensioned to snugly engage spherical portion 12 of facet dowel 10. A pair of opposed slots 4e allow some flexing of the inserter tip, so that dowel 10 may be partially inserted into tip 4a with nose portion pointed forward and outside of the tip area and with tail portion up in the channel as seen in FIGS. 10E and 10F. A set of four annular holes 4f are provided for allowing the tip to flex and receive the implant or allograft.

With the working channel in place as seen in FIGS. 10E and 10F and with the legs 1d and 1e stabilizing and locating the working channel with respect to the inter-facet gap or space in ways known in the art, the inserter, with the allograft 10 (nose portion forward) may be inserted into the working channel and moved to the shaped site for inserting, typically by gentle tamping, therein.

FIG. 7 illustrates a driver tamp 5 for the uses set forth herein. Driver tamp 5 is seen to have a tip portion 5a, a cylindrically elongated body 5b, and a stop portion 5c at a removed end thereof. Tip 5a and body 5b are dimensioned for receipt within the inner channel of the inserter with a length between the near end of face walls of stop 5c and the removed end at tip 5a, here designated as about 165.84 mm. When inserter 4 is fully seated into working channel 1 (stop 4c flush with end walls of working channel), with the allograft in the proper position on the tip thereof, and when driver tamp 5 is fully inserted such that stop 5c is against stop 4c, removed tip 5a will have pushed tail 16 of the allograft to the position illustrated in FIG. 10F, that is, fully inserted.

FIGS. 8A and 8B illustrate joint finder 7 having a tip portion 7a, cylindrical elongated body portion 7b, and removed end 7c. Tip portion 7a is tabular with a wedge-shaped removed end as seen in FIG. 8A and the body portion is long enough to receive the working channel over it as seen in FIG. 10B. Boss 7d is provided for alignment and engagement with slot 1j as seen in FIG. 10B1.

Channel set 8 is seen to have a cylindrical, hollow channel 8a therein. Channel set 8 is further seen to have a nose portion 8b extending from a body portion 8c, both portions 8a and 8b being cylindrical and having inner walls which define hollow channel 8a. Body 8c is seen to have forward stop 8d between nose portion 8b and body portion 8c.

FIGS. 10A-10F help illustrate the structure and function of the foregoing instruments and allograft as used in a facet joint fusion operation.

A brief summary of the steps used to implant the allograft to assist in the fusion, which implanted allograft is illustrated in FIG. 11, is set forth as follows. After opening and preparing the surgical site in ways known in the art, the facet finder is tapped into position until minimal resistance is met as seen in FIG. 10A. Next, the working channel is slid down the joint finder. Alignment pins (legs) are utilized for the placement of the working channel over the facet finder and tapped into place until seated on the facet. This is illustrated in FIG. 10B, FIG. 10B1 shows the alignment of the pins in the channel. Next, the drill is inserted into the working channel and the drilling is continued through the working channel until the drill hits the stop. This is illustrated in FIG. 10C.

FIGS. 10D, 10D1, 10D2, and 10D3 illustrate the step in which the drilled-out channel is further excavated through the use of a T-spade. The T-spade drill is laser marked and the T-spade drill and the working channel are aligned in parallel to the facet joint as seen in FIG. 10D1. The drill is rotated two or three times until no resistance (see FIG. 10D2), which illustrates the tip of the T-spade drill when it is rotated perpendicular to the aligned position or the parallel position as set forth in FIG. 10D1.

FIG. 10D3 illustrates the excavated space and the T-spade drill in the aligned position, which will allow the withdrawal of the instrument from the working channel.

Next, the allograft 10 is loaded into inserter 4 and moved to the insertion site, which has been drilled and excavated. The inserter is then placed into the working channel, with the allograft on the tip until the inserter is flush with the channel instrument (see FIG. 10E). A tamp is placed through the central channel of the inserter until it touches the removed end of the tail of the allograft, at which point the allograft is tapped into a final position as illustrated in FIG. 11 (see also FIG. 10F).

In FIG. 10A, a superior and inferior facet is seen and joint finder 7 is used to locate and, if necessary, separate slightly interior and inferior facet. The proper angle, depth, and spacing of the facets and how to manipulate the joint finder would be apparent to one skilled in the art.

After the site is located and prepared by the joint finder in ways known in the art, then the working channel 1 is slipped over the joint finder as is illustrated in FIG. 10B. The working channel may be manipulated by rotating it slightly while urging it into the joint as located by the joint finder. The legs of the working channel will typically be parallel to and in the plane of the face of the wedge-shaped tip as best seen in FIG. 10B. Channel set 8 may be slipped over the removed end of the joint finder and tapped so as to drive the legs and the working channel snugly into the inter-facet gap area and to locate the working channel at the allograft site location.

FIGS. 8A, 10B, and 10B1 also illustrate that a boss 7d may be provided for engaging a slot 1j at the end of channel 1 so the legs of the channel align with the flat of the wedge on the joint finder. The boss may be dimensioned so as to fit within the interior of the working channel.

FIG. 10C illustrates the step of drilling the allograft site (following removal of the joint finder from the working channel). Moreover, it may be appreciated how the stop member on the prep-drill is used to limit the penetration of the drill tip beyond a selective limit past end walls 1i of working channel 1. A T-handle 18 may be used to engage the hex end of the prep-drill in ways known in the art.

FIGS. 10D-10D3 illustrate the shaping step wherein the T-spade drill 3 is inserted into the working channel and extended with orientation boss 3j through longitudinal slot 1e, which orientation of the boss in the slot will place the flat portion of parallel to the faces of the interior and superior facets, which are adjacent the inter-facet space. Moreover, it is seen that orientation slot 1e on the working channel is located aligned the legs 1e of the working channel 1, which legs define the plane in which the flat portion 3g of the T-spade drill 3 is placed when the T-spade drill 3 is urged up to the facet joint. Rotation of 180° in either direction will then allow the spherical leading edge defining the outer perimeter of the flat portion 3g to shape the vertebrae bone above and below the drilled out channel in such a way as to provide a fit for the allograft as best seen in the detailed portion of FIG. 10D.

FIG. 10E illustrates the manner in which the allograft 10, with its tail inserted in the tip portion 4a of inserter 4, is urged so that the nose and typically a portion of spherical body 12 is protruding from end walls 1i as best seen in the detail in FIG. 10E. When this position is reached, the stop portion 4e of the inserter 4 is typically up against the removed end of working channel 1 as seen in FIG. 10F.

At this point, as illustrated in FIG. 10F, the driver tamp 5 may be inserted in the inner channel of the inserter 4 until strikes the removed end of the tail of the allograft. At that point, it may be struck or otherwise pushed, while holding the channel set and such action will force the spherical body to spread the two facets slightly until the spherical body reaches the shaped interior of volume corresponding to the spherical shape excavated as illustrated in FIG. 10D. At this point, the inferior and superior facet faces will, under compression, close around the spherical body in the manner illustrated in the detailed portion of FIG. 10F.

Although the invention has been described in connection with the preferred embodiment, it is not intended to limit the invention's particular form set forth, but on the contrary, it is intended to cover such alterations, modifications, and equivalences that may be included in the spirit and scope of the invention as defined by the appended claims. For example, gas is considered to be a fluid, the device may operate with either a liquid or a gas.

The invention claimed is:

1. An implant configured for receipt between opposing spinal facets, the implant comprising:
a substantially rigid spherical segment having a diameter Ds and an outer surface;
a tail segment comprising a cylindrical shape and an outer surface, the cylindrical shape joined at a first end and integral to the spherical segment and having a removed end, the tail segment having a longitudinal axis, a diameter Dt, and a length $L_T$;
a nose segment comprising a cylindrical shaped portion, a cap at a removed end of the cylindrical shaped portion, and an outer surface, the nose segment adapted to guide the spherical segment and the tail segment between inner faces of opposing spinal facets during insertion of the implant, the nose segment integral with the spherical segment at a near end, the nose segment having a length Ln, a longitudinal axis coincident with the longitudinal axis of the tail segment, and a diameter Dn;
wherein the implant is composed essentially of bone and the outer surfaces of the spherical segment, the tail segment, and the nose form an external surface for the implant, substantially the entire external surface being smooth.

2. The implant of claim 1, wherein the length of the tail is between about 1-3 mm.

3. The implant of claim 1, wherein the length of the nose is between about 1-3 mm.

4. The implant of claim 1, wherein the length of the spherical segment along the longitudinal axis thereof is about 2.5-6.5 mm.

5. The implant of claim 1, wherein the overall length is between about 6.5 mm and 10.5 mm.

6. The implant of claim 1, wherein the diameter of the tail is between about 1.8-5.8 mm.

7. The implant of claim 1, wherein the diameter of the nose is between about 1.8-5.8 mm.

8. The implant of claim 1, wherein the diameter of the spherical segment is between about 3.8-7.8 mm and the thickness is between about 0.52 and 2.52 mm.

9. The implant of claim 1, wherein the entire external surface is smooth; wherein the length of the tail is between about 1-3 mm; and wherein the diameter of the tail is between about 1.8-5.8 mm.

10. The implant of claim 1, wherein the entire external surface is smooth; wherein the length of the nose is between about 1-3 mm; and wherein the diameter of the nose is between about 1.8-5.8 mm.

11. The implant of claim 1, wherein the entire external surface is smooth; wherein the length of the spherical segment along the longitudinal axis thereof is about 2.5-6.5 mm; and wherein the diameter of the spherical segment is between about 3.8-7.8 mm.

12. The implant of claim 1, wherein the entire external surface is smooth; wherein the length of the tail is between about 1-3 mm; wherein the length of the nose is between about 1-3 mm; wherein the length of the spherical segment along the longitudinal axis thereof is about 2.5-6.5 mm; wherein the diameter of the tail is between about 1.8-5.8 mm; wherein the diameter of the nose is between about 1.8-5.8 mm; and wherein the diameter of the spherical segment is between about 3.8-7.8 mm.

13. The implant of claim 1, wherein the implant is a bone allograft.

14. The implant of claim 1, wherein the longitudinal axes are aligned substantially parallel to inner faces of spinal facets when the implant is inserted.

15. The implant of claim 1, wherein the cap is adapted to burrow between inner faces of spinal facets during insertion of the implant.

16. The implant of claim 1, wherein the spherical segment is adapted to be wider than perpendicular distances between portions of the substantially parallel inner faces of the opposing facets in the vicinity of the spherical segment after insertion of the implant.

17. The implant of claim 1, wherein the spherical segment is adapted to be more than 2.5 mm wider than perpendicular distances between portions of substantially parallel inner faces of the opposing facets in the vicinity of the spherical segment after insertion of the implant.

18. An insert configured for receipt between an upper facet and a spaced apart lower facet, the upper and lower facets having a drilled out cylindrical channel between inner faces of the facets, wherein part of the inner face of the upper facet comprises part of the cylindrical wall and part of the inner face of the lower facet comprises an opposing part of the cylindrical wall, the facets further having walls defining a spherical segment opening, the insert comprising:
  a substantially rigid spherical segment having walls, the spherical segment adapted to sit snuggly and at least partly against the walls defining the spherical segment opening;
  a generally cylindrical tail segment having outer walls adapted to sit at least partially against walls defining the cylindrical channel; and
  an at least partly cylindrical nose segment having outer walls adapted to sit snuggly and at least partially against walls defining the cylindrical channel;
  wherein the insert is composed essentially of bone and the walls of the segments define an external surface for the insert, substantially the entire external surface being smooth.

19. The insert of claim 18, wherein the entire external surface is substantially smooth.

20. The insert of claim 19, wherein the length of the tail is between about 1-3 mm; wherein the length of the nose is between about 1-3 mm; wherein the length of the spherical segment along the longitudinal axis thereof is about 2.5-6.5 mm; wherein the diameter of the tail is between about 1.8-5.8 mm; wherein the diameter of the nose is between about 1.8-5.8 mm; wherein the length overall is between about 6.5-10.5 mm; and wherein the diameter of the spherical segment is between about 3.8-7.8 mm.

21. The insert of claim 18, wherein the insert is a bone allograft.

22. The insert of claim 18, wherein a longitudinal axis that passes through the spherical segment, the nose segment, and the tail segment is aligned substantially parallel to the inner faces of the facets when the insert is inserted.

23. The insert of claim 18, wherein the nose segment is adapted to guide the spherical segment and the tail segment in the channel during insertion of the insert.

24. The insert of claim 18, wherein the nose segment is adapted to burrow in the cylindrical channel during insertion of the insert.

25. The insert of claim 18, wherein the spherical segment is adapted to be wider than perpendicular distances between portions of the substantially parallel inner faces of the spinal facets in the vicinity of the spherical segment after insertion of the insert.

26. The insert of claim 18, wherein the spherical segment is adapted to be more than 2.5 mm wider than perpendicular distances between portions of substantially parallel inner faces of the spinal facets in the vicinity of the spherical segment after insertion of the insert.

* * * * *